US012369583B2

(12) United States Patent
Jenni et al.

(10) Patent No.: US 12,369,583 B2
(45) Date of Patent: Jul. 29, 2025

(54) NEMATICIDAL COMPOSITIONS

(71) Applicant: SYNGENTA CROP PROTECTION AG, Basel (CH)

(72) Inventors: Domenica Jenni, Stein (CH); Brigitte Slaats, Basel (CH); Ana Cristina Dutton, Basel (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 975 days.

(21) Appl. No.: 17/414,623

(22) PCT Filed: Dec. 23, 2019

(86) PCT No.: PCT/EP2019/086912
§ 371 (c)(1),
(2) Date: Jun. 16, 2021

(87) PCT Pub. No.: WO2020/128091
PCT Pub. Date: Jun. 25, 2020

(65) Prior Publication Data
US 2022/0061322 A1 Mar. 3, 2022

(30) Foreign Application Priority Data
Dec. 21, 2018 (GB) ..................................... 1821036

(51) Int. Cl.
*A01N 43/56* (2006.01)
*A01N 25/04* (2006.01)
*A01P 5/00* (2006.01)

(52) U.S. Cl.
CPC ............. *A01N 43/56* (2013.01); *A01N 25/04* (2013.01); *A01P 5/00* (2021.08)

(58) Field of Classification Search
CPC ..................................................... A01N 43/56
See application file for complete search history.

(56) References Cited

U.S. PATENT DOCUMENTS

| 8,258,169 | B2 | 9/2012 | Rajan et al. |
| 10,869,476 | B2 | 12/2020 | Dahmen et al. |
| 2016/0270394 | A1 | 9/2016 | Hungenberg et al. |

FOREIGN PATENT DOCUMENTS

| CN | 102239137 A | 11/2011 |
| CN | 106857540 A | 6/2017 |
| CN | 107396929 A | 11/2017 |
| EP | 3292759 A1 | 3/2018 |
| JP | 2018531254 A | 10/2018 |
| WO | 2010063700 A2 | 6/2010 |
| WO | 2012072660 A1 | 6/2012 |
| WO | 2014177514 A1 | 11/2014 |
| WO | 2017093163 A1 | 6/2017 |
| WO | 2018069114 A1 | 4/2018 |

OTHER PUBLICATIONS

Haouchine, et al., "First evidence of human infection by *Xiphinema brevicollum* (Nematoda: Longidoridae)", International Journal of Infectious Diseases, vol. 122, pp. 609-611, 2022.
Murillo-Williams, et al., "Plant Parasitic Nematodes Explained", Mar. 31, 2023, pp. 1-3; Retrieved from the internet, URL:https://extension.psu.edu/plant-parasitic-nematodes•explained.
Faske et al., Sensitivity of Meloidogyne Incognita and Rotylenchulus Reniformis to Fluopyram, Journal of Nematology, vol. 47, Issue (4), Dec. 1, 2015, pp. 316-321.
GB Search Report for GB application No. GB1821036.9, mailed Jun. 11, 2019.
MDA State, Pydiflumetofen, New Active Ingredient Review, Jun. 1, 2018, pp. 1-2.
Hou et al., Sensitivity of Fusarium Asiaticum to a Novel Succinate Dehaydrogenase Inhibitor Fungicide Pydiflumetofen, Crop Protection Elsevier Science, GB vol. 96, Mar. 6, 2017, pp. 237-244.
Written Opinion of the International Searching Authority and International Search Report for application No. PCT/EP2019/086912 mailed May 7, 2020.
Throssell, "Closer Look: Indemnify, a New Nematode Control Product", Golfdom, Oct. 24, 2016, pp. 1-2.

*Primary Examiner* — Shawquia Jackson
(74) *Attorney, Agent, or Firm* — BakerHostetler; Toni-Junell Herbert

(57) ABSTRACT

The present invention relates to the use of N-methoxy (phenylethyl)-pyrazole carboxamides for the control of nematodes in agriculture and as antihelminthic agents against endoparasites in animals and humans, as well as compositions comprising such compounds. The present invention 5 further relates to the use of these compounds or compositions for controlling nematodes and/or helminths, in particular for controlling plant parasitic nematodes, and to the use of these compounds in preparing nematicidal and/or antihelminthic compositions.

14 Claims, No Drawings

NEMATICIDAL COMPOSITIONS

CROSS-REFERENCE TO RELATED APPLICATIONS

This application is a 371 National Stage application of International Application No. PCT/EP2019/086912 filed Dec. 23, 2019, claims priority to GB 1821036.9 filed Dec. 21, 2018, the entire contents of these applications are hereby incorporated by reference.

The present invention relates to the use of N-methoxy (phenylethyl)-pyrazole carboxamides for the control of nematodes in agriculture and as antihelminthic agents against endoparasites in animals and humans, as well as compositions comprising such compounds. The present invention further relates to the use of these compounds or compositions for controlling nematodes and/or helminths, in particular for controlling plant parasitic nematodes, and to the use of these compounds in preparing nematicidal and/or antihelminthic compositions.

Plant parasitic nematodes, many of which are root feeders, are found in association with most plants. Whilst some are ectoparasitic, feeding externally through plant walls, others are endoparasitic, living and feeding within plant tissue, for example roots, tubers, buds, seeds and the like. Economically important pests include some key endoparasitic root feeders, for example, the rootknot nematodes (*Meloidogyne* species), the reniform nematodes (*Rotylenchulus* species), the cyst nematodes (*Heterodera* species) and the root lesion nematodes (Pratylenchus species). Damage to plants may be direct, in that feeding by a nematode may result in a reduction in nutrient and water uptake within the plant, or indirect, in that feeding creates wounds within a plant, and these are susceptible to secondary pathogenic infection by bacteria, viruses and/or fungi. Since a single nematode is capable of either killing or having a significant adverse effect on the productivity of a plant, it can be seen that nematode control within the agricultural and horticultural industry is clearly desirable. Typically this achieved addressed through the use of chemical compounds having nematicidal activity. Ideally such compounds should have a high activity, a broad-spectrum activity against different strains of nematodes and should not be toxic to non-target organism.

The compound 3-(difluoromethyl)-N-methoxy-1-methyl-N-[1-methyl-2-(2,4,6-trichloro-phenyl)ethyl]-1H-pyrazole-4-carboxamide (pydiflumetofen) described in WO2010/063700 is a new broad-spectrum foliar fungicide and the first example of the new group of N-methoxy-(phenylethyl)-pyrazole-carboxamides within the succinate dehydrogenase inhibitors (SDHI). The present invention is based on the surprising finding that 3-(difluoromethyl)-N-methoxy-1-methyl-N-[1-methyl-2-(2,4,6-trichloro-phenyl)ethyl]-1H-pyrazole-4-carboxamide also exhibits anti-nematode activity and can thus now be employed in the fight against nematodes and/or endoparasites in animals or humans.

Thus, in a first aspect the present invention relates to the use of 3-(difluoromethyl)-N-methoxy-1-methyl-N-[1-methyl-2-(2,4,6-trichloro-phenyl)ethyl]-1H-pyrazole-4-carboxamide, or an agrochemically acceptable salt, isomer, stereoisomer, diastereoisomer, enantiomer or tautomer thereof, to control nematodes.

In a second aspect, there is provided a method of controlling a plant parasitic nematode, said method comprising applying an effective amount of 3-(difluoromethyl)-N-methoxy-1-methyl-N-[1-methyl-2-(2,4,6-trichloro-phenyl) ethyl]-1H-pyrazole-4-carboxamide, to the plant parasitic nematode, or to the locus of the plant parasitic nematode.

In a third aspect, there is provided a method of controlling infestation of a useful plant by a plant parasitic nematode, said method comprising applying an effective amount of 3-(difluoromethyl)-N-methoxy-1-methyl-N-[1-methyl-2-(2, 4,6-trichloro-phenyl)ethyl]-1H-pyrazole-4-carboxamide to the plant seed or the plant roots of the useful plant prior to planting.

In a fourth aspect there is provided plant propagation material having adhered thereto, 3-(difluoromethyl)-N-methoxy-1-methyl-N-[1-methyl-2-(2,4,6-trichloro-phenyl) ethyl]-1H-pyrazole-4-carboxamide, such that said plant propagation material generates a plant free from nematode infection upon propagation.

In a fifth aspect there is provided a pharmaceutical composition for the control of helminths, or arthropodal endo- or ectoparasites which comprises 3-(difluoromethyl)-N-methoxy-1-methyl-N-[1-methyl-2-(2,4,6-trichloro-phenyl)ethyl]-1H-pyrazole-4-carboxamide, a physiologically tolerable carrier and optionally one or more customary formulation auxiliaries.

In a sixth aspect there is provided a pharmaceutical composition comprising 3-(difluoromethyl)-N-methoxy-1-methyl-N-[1-methyl-2-(2,4,6-trichloro-phenyl)ethyl]-1H-pyrazole-4-carboxamide, a physiologically tolerable carrier, and optionally one or more customary formulation auxiliaries for preventing infection with, and/or diseases transmitted through, helminths, or arthropodal endo- or ectoparasites.

3-(Difluoromethyl)-N-methoxy-1-methyl-N-[1-methyl-2-(2,4,6-trichloro-phenyl)ethyl]-1H-pyrazole-4-carboxamide and its preparation are described in WO2010/063700, WO2013/127764, and WO2014/206855. The skilled man will appreciate that 3-(difluoromethyl)-N-methoxy-1-methyl-N-[1-methyl-2-(2,4,6-trichloro-phenyl)ethyl]-1H-pyrazole-4-carboxamide exists in two enantiomeric forms: 3-(difluoromethyl)-N-methoxy-1-methyl-N-[(1R)-1-methyl-2-(2,4,6-trichloro-phenyl)ethyl]-1H-pyrazole-4-carboxamide and 3-(difluoromethyl)-N-methoxy-1-methyl-N-[(1S)-1-methyl-2-(2,4,6-trichloro-phenyl)ethyl]-1H-pyrazole-4-carboxamide. Both enantiomers can be used for the control of nematodes according to the invention, individually, or as a racemate. The compound 3-(difluoromethyl)-N-methoxy-1-methyl-N-[1-methyl-2-(2,4,6-trichloro-phenyl)ethyl]-1H-pyrazole-4-carboxamide may be referred to herein by full name, or in the alternative as "the compound".

As described herein, the present invention relates to methods for controlling nematodes typically comprising the application of 3-(difluoromethyl)-N-methoxy-1-methyl-N-[1-methyl-2-(2,4,6-trichloro-phenyl)ethyl]-1H-pyrazole-4-carboxamide to an organism to be protected, or its locus, in an effective amount to act on the nematode. Such methods are particularly suitable to nematodes which are plant parasitic nematodes located in the soil; accordingly, such methods include application of -(difluoromethyl)-N-methoxy-1-methyl-N-[1-methyl-2-(2,4,6-trichloro-phenyl)ethyl]-1H-pyrazole-4-carboxamide to the soil, or to the roots, seeds or other plant propagation material of useful plants.

As used herein the term "useful plants" typically includes plants of the following species: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; rice; maize; tobacco; nuts; coffee; sugar cane; tea; vines; hops; durian; bananas; natural rubber plants; turf or ornamentals, such as flowers, shrubs, broad-leaved trees or evergreens, for example conifers. This above list does not represent any limitation. However, particularly preferred useful plants include soybean, wheat, maize, or cotton.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF (a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and Sesamia nonagrioides) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. kurstaki which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "useful plants" is to be understood as also including those plants which have been transformed by the use of recombinant DNA techniques such that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Useful plants of particular interest in connection with present invention include those of agronomic interest such as for example, cereals, soybean, cotton, peanut, sorghum; vegetables, such as, for example, beans, maize, carrot, crucifers, tomato, potato, sugar beet; fruit, such as, for example, citrus, strawberries, vines; turfgrasses; and forest crops (e.g. pine trees).

Useful plants also include those which exhibit a degree of endogenous resistance to nematodes, as well as those engineered to have an increase in resistance to nematodes. In such a case, the application of 3-(difluoromethyl)-N-methoxy-1-methyl-N-[1-methyl-2-(2,4,6-trichloro-phenyl)ethyl]-1H-pyrazole-4-carboxamide is complementary.

The term "locus" of a useful plant as used herein is intended to embrace the place on which the useful plants are growing, where the plant propagation materials of the useful plants are sown or where the plant propagation materials of the useful plants will be placed for growth, e.g. soil. An example for such a locus is the soil in, for example, a field on which crop plants are growing.

The term "plant propagation material" as used herein is understood to denote generative parts of a useful plant, such as seeds, which can be used for the multiplication of the latter, and vegetative material, such as cuttings or tubers, for example potatoes. There may be mentioned for example seeds (in the strict sense), roots, fruits, tubers, bulbs, corms, rhizomes and parts of plants. Germinated plants and young plants which are to be transplanted after germination or after emergence from the soil, may also be mentioned. These young plants may be protected before transplantation by a total or partial treatment by immersion in the compound. Preferably "plant propagation material" is understood to denote seeds and/or roots, more preferably seeds.

The term "nematicide" as used herein with respect to 3-(difluoromethyl)-N-methoxy-1-methyl-N-[1-methyl-2-(2,4,6-trichloro-phenyl)ethyl]-1H-pyrazole-4-carboxamide means that the compound is capable of controlling nematodes.

In order to control nematodes, 3-(difluoromethyl)-N-methoxy-1-methyl-N-[1-methyl-2-(2,4,6-trichloro-phenyl)ethyl]-1H-pyrazole-4-carboxamide, is applied or administered in an "effective amount", by which is meant any amount of 3-(difluoromethyl)-N-methoxy-1-methyl-N-[1-methyl-2-(2,4,6-trichloro-phenyl)ethyl]-1H-pyrazole-4-carboxamide that, upon suitable application, is sufficient to achieve the desired level of nematode control.

The phrase "controlling nematodes" as used herein means killing nematodes or preventing nematodes from developing or growing. The term also encompasses controlling nematode progeny (development of viable cysts and/or egg masses). The compound 3-(difluoromethyl)-N-methoxy-1-methyl-N-[1-methyl-2-(2,4,6-trichloro-phenyl)ethyl]-1H-pyrazole-4-carboxamide may be used to keep an organism healthy and may be used curatively, preventively or systematically to control nematodes.

An "organism" as mentioned in the above paragraphs may be a plant. When using the 3-(difluoromethyl)-N-methoxy-1-methyl-N-[1-methyl-2-(2,4,6-trichloro-phenyl)ethyl]-1H-pyrazole-4-carboxamide to keep a plant healthy, the control of nematodes reduces damage to plants and thus may results in a concomitant increase in yield.

Alternatively, the organisms as mentioned above may be a human or an animal. When using 3-(difluoromethyl)-N-methoxy-1-methyl-N-[1-methyl-2-(2,4,6-trichloro-phenyl)ethyl]-1H-pyrazole-4-carboxamide described herein to keep a human or animal healthy, the use encompasses therapeutic use and veterinarian use with the aim to prevent or to cure damage by nematodes.

The efficacy of 3-(difluoromethyl)-N-methoxy-1-methyl-N-[1-methyl-2-(2,4,6-trichloro-phenyl)ethyl]-1H-pyrazole-4-carboxamide against plant parasitic nematodes may be assessed by comparing the mortality of nematodes, the development of galls, the formation of cysts, the concentration of nematodes per volume of soil, of cysts, the concentration of nematodes per root, the number of nematode eggs per volume of soil, the motility of the nematodes between a plant, a plant part or the soil treated with 3-(difluoromethyl)-N-methoxy-1-methyl-N-[1-methyl-2-(2,4,6-trichloro-phenyl)ethyl]-1H-pyrazole-4-carboxamide according to the invention and the untreated plant, plant part or soil (100 percent). The skilled person is familiar with such methods, and further details for various methods are given below, in the Examples.

As mentioned supra, the present invention addresses the need to control plant parasitic nematodes. The term "nematodes" as used herein encompass all species of the phylum Nematoda and in particular species that are parasitic or cause health problems to a plant (for example species of the orders Aphelenchida, *Meloidogyne*, Tylenchida and others) or to humans and animals (for example species of the orders Trichinellida, Tylenchida, Rhabditina, and Spirurida) as well as other parasitic helminths.

Plant nematodes include plant parasitic nematodes and nematodes living in the soil that cause damage to plants.

Plant parasitic nematodes include, but are not limited to, ectoparasites such as Xiphinema spp., *Longidorus* spp., and Trichodorus spp.; semiparasites such as *Tylenchulus* spp.; migratory endoparasites such as Pratylenchus spp., *Radopholus* spp., and Scutellonema spp.; sedentary parasites such as Heterodera spp., Globodera spp., and Meloidogyne spp., and stem and leaf endoparasites such as Ditylenchus spp., Aphelenchoides spp., and Hirshmaniella spp.

Especially harmful root parasitic soil nematodes are such as cystforming nematodes of the genera *Heterodera* or *Globodera*, and/or root knot nematodes of the genus *Meloidogyne*.

Harmful species of these genera are for example *Meloidogyne incognita*, *Heterodera glycines* (soybean cyst nematode), *Globodera pallida* and *Globodera rostochiensis* (potato cyst nematode), which may be controlled by the compound according to the invention.

However, the use of 3-(difluoromethyl)-N-methoxy-1-methyl-N-[1-methyl-2-(2,4,6-trichloro-phenyl)ethyl]-1H-pyrazole-4-carboxamide is in no way restricted to these genera or species, but also extends in the same manner to other nematodes.

Plant nematodes include (but are not limited to): Aglenchus *agricola*, *Anguina tritici*, *Aphelenchoides arachidis*, *Aphelenchoides fragaria* and *Aphelenchoides* spp. in general; *Belonolaimus gracilis*, *Belonolaimus longicaudatus*, *Belonolaimus nortoni*. *Bursaphelenchus cocophilus*, *Bursaphelenchus eremus*, *Bursaphelenchus xylophilus* and *Bursaphelenchus* spp. in general; Cacopaurus *pestis*, Criconemella *curvata*, Criconemella *onoensis*, Criconemella *ornata*, Criconemella *rusium*, Criconemella *xenoplax* (=Mesocriconema xenoplax) and Criconemella spp. in general; Criconemoides *ferniae*, Criconemoides *onoense*, Criconemoides *ornatum* and Criconemoides spp. in general; *Ditylenchus destructor, Ditylenchus dipsaci, Ditylenchus myceliophagus* and *Ditylenchus* spp. in general; Dolichodorus *heterocephalus*, *Globodera pallida* (=*Heterodera pallida*), *Globodera rostochiensis* (potato cyst nematode), *Globodera solanacearum*, *Globodera tabacum*, *Globodera Virginia*, and *Globodera* spp. in general; Helicotylenchus *digonicus*, Helicotylenchus *dihystera*, Helicotylenchus *erythrine*, Helicotylenchus *multicinctus*, Helicotylenchus *nannus*, Helicotylenchus *pseudorobustus* and Helicotylenchus spp. in general; Hemicriconemoides, Hemicycliophora *arenaria*, Hemicycliophora *nudata*, Hemicycliophora *parvana*, Heterodera *avenae*, Heterodera *cruciferae*, Heterodera *glycines* (soybean cyst nematode), *Heterodera oryzae*, *Heterodera schachtii*, *Heterodera zeae* and *Heterodera* spp. in general; Hirschmaniella *gracilis*, Hirschmaniella *oryzae* Hirschmaniella *spinicaudata* and Hirschmaniella spp., Hoplolaimus aegyptii, Hoplolaimus *californicus*, Hoplolaimus *columbus*, Hoplolaimus *galeatus*, Hoplolaimus *indicus*, Hoplolaimus magnistylus, Hoplolaimus *pararobustus, Longidorus africanus, Longidorus breviannulatus, Longidorus elongatus, Longidorus laevicapitatus, Longidorus* vineacola and *Longidorus* spp. in general; *Meloidogyne* acronea, *Meloidogyne africana*, *Meloidogyne arenaria, Meloidogyne arenaria* thamesi, *Meloidogyne* artiella, *Meloidogyne* chitwoodi, *Meloidogyne coffeicola*, *Meloidogyne ethiopica*, *Meloidogyne exigua*, *Meloidogyne fallax*, *Meloidogyne graminicola*, *Meloidogyne graminis*, *Meloidogyne hapla*, *Meloidogyne incognita*, *Meloidogyne incognita acrita*, *Meloidogyne javanica*, *Meloidogyne kikuyensis*, *Meloidogyne minor, Meloidogyne naasi, Meloidogyne paranaensis, Meloidogyne* thamesi and *Meloidogyne* spp. in general; Meloinema spp.; Nacobbus *aberrans*, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres and Paratrichodorus spp in general; Paratylenchus *hamatus*, Paratylenchus *minutus*, Paratylenchus *projectus* and Paratylenchus spp. in general; Pratylenchus *agilis*, Pratylenchus *alleni*, Pratylenchus *andinus*, Pratylenchus *brachyurus*, Pratylenchus *cerealis*, Pratylenchus *coffeae*, Pratylenchus *crenatus*, Pratylenchus *delattrei*, Pratylenchus giibbicaudatus, Pratylenchus goodeyi, Pratylenchus *hamatus*, Pratylenchus hexincisus, Pratylenchus *loosi*, Pratylenchus *neglectus*, Pratylenchus *penetrans*, Pratylenchus *pratensis*, Pratylenchus *scribneri*, Pratylenchus *teres*, Pratylenchus *thornei*, Pratylenchus *vulnus*, Pratylenchus *zeae* and Pratylenchus spp. in general; Pseudohalenchus *minutus*, Psilenchus *magnidens*, Psilenchus *tumidus*, Punctodera *chalcoensis*, Quinisulcius *acutus*, Radopholus *citrophilus*, Radopholus *similis*, and Radopholus spp. in general; Rotylenchulus *borealis*, *Rotylenchulus parvus*, *Rotylenchulus reniformis* and *Rotylenchulus* spp. in general; Rotylenchus *laurentinus*, Rotylenchus *macrodoratus*, Rotylenchus *robustus*, Rotylenchus *uniformis* and Rotylenchus spp. in general; Scutellonema *brachyurum*, Scutellonema bradys, Scutellonema clathricaudatum and Scutellonema spp. in general; Subanguina radiciola, Tetylenchus *nicotianae*, Trichodorus *cylindricus*, Trichodorus *minor*, Trichodorus *primitivus*, Trichodorus *proximus*, Trichodorus *similis*, Trichodorus *sparsus* and Trichodorus spp. in general; Tylenchorhynchus *agri*, Tylenchorhynchus *brassicae*, Tylenchorhynchus *clarus*, Tylenchorhynchus *claytoni*, Tylenchorhynchus *digitatus*, Tylenchorhynchus *ebriensis*, Tylenchorhynchus *maximus*, Tylenchorhynchus *nudus*, Tylenchorhynchus *vulgaris* and Tylenchorhynchus spp. in general; Tylenchulus semipenetrans and Tylenchulus spp. in general; Xiphinema *americanum*, Xiphinema *brevicolle*, Xiphinema dimorphicaudatum, Xiphinema *index* and Xiphinema spp. in general.

Examples of nematodes to which 3-(difluoromethyl)-N-methoxy-1-methyl-N-[1-methyl-2-(2,4,6-trichloro-phenyl)ethyl]-1H-pyrazole-4-carboxamide is applicable include, but are not limited to, nematodes of the genus *Meloidogyne* such as the southern root-knot nematode (*Meloidogyne incognita*), Javanese root-knot nematode (*Meloidogyne javanica*), northern root-knot nematode (*Meloidogyne hapla*), and peanut root-knot nematode (*Meloidogyne arenaria*); nematodes of the genus *Ditylenchus* such as the potato rot nematode (*Ditylenchus destructor*) and bulb and stem nematode (*Ditylenchus dipsaci*); nematodes of the genus Pratylenchus such as the cob root-lesion nematode (Pratylenchus *penetrans*), *chrysanthemum* root-lesion nematode (Pratylenchus *fallax*), coffee root-lesion nematode (Pratylenchus *coffeae*), tea root-lesion nematode (Pratylenchus *loosi*), and walnut root-lesion nematode (Pratylenchus *vulnus*); nematodes of the genus *Globodera* such as the golden nematode (*Globodera rostochiensis*) and potato cyst nematode (*Globodera pallida*); nematodes of the genus *Heterodera* such as the soybean cyst nematode (*Heterodera glycines*) and sugar beet cyst nematode (*Heterodera schachtii*); nematodes of the genus *Aphelenchoides* such as the rice white-tip nematode (*Aphelenchoides besseyi*), *chrysanthemum* foliar nematode (*Aphelenchoides* ritzemabosi), and strawberry nematode (*Aphelenchoides fragariae*); nematodes of the genus Aphelenchus such as the mycophagous nematode (Aphelenchus *avenae*); nematodes of the genus *Radopholus* such as the burrowing nematode (*Radopholus similis*); nematodes of the genus *Tylenchulus* such as the citrus nematode (*Tylenchulus semipenetrans*); nematodes of the genus *Rotylenchulus* such as the reniform nematode (*Rotylenchulus reniformis*); nematodes that occur in trees, such as the pine wood nematode (*Bursaphelenchus xylophilus*), and the like.

It is preferred that 3-(difluoromethyl)-N-methoxy-1-methyl-N-[1-methyl-2-(2,4,6-trichloro-phenyl)ethyl]-1H-pyrazole-4-carboxamide is used for the control of the following species: *Heterodera* spp, *Meloidogyne* spp, Pratylenchus spp, *Rotylenchulus* spp, *Belonolaimus* spp, Hoplolaimus spp., Xiphinema spp (dagger nematode), *Longidorus* spp, (needle nematode) Mesocriconema spp. (ring nematode), Hemicycliophora spp. (sheath nematode), Heliotylenchus spp. (spiral nematode), Paratrichodorus spp. (stubby root nematode), and Tylenchorhynchus spp. (stunt nematode). It is particularly preferred that 3-(difluoromethyl)-N-methoxy-1-methyl-N-[1-methyl-2-(2,4,6-trichloro-phenyl)ethyl]-1H-pyrazole-4-carboxamide is used for the control of *Heterodera* spp, *Meloidogyne* spp, Pratylenchus spp, *Rotylenchulus* spp, *Belonolaimus* spp, and Hoplolaimus spp.

As shown herein, 3-(difluoromethyl)-N-methoxy-1-methyl-N-[1-methyl-2-(2,4,6-trichloro-phenyl)ethyl]-1H-pyrazole-4-carboxamide is particularly efficacious against soybean cyst nematode (*Heterodera glycines*), root knot nematode (*Meloidogyne incognita*), lesion nematode (Pratylenchus *brachyurus*), reniform nematode (*Rotylenchulus reniformis*), Sting nematode (*Belonolaimus longicaudatus*) and Lance nematode (Hoplolaimus spp.).

The compound 3-(difluoromethyl)-N-methoxy-1-methyl-N-[1-methyl-2-(2,4,6-trichloro-phenyl)ethyl]-1H-pyrazole-4-carboxamide may be employed for nematode control in can be used in unmodified form or, preferably, together with carriers and adjuvants conventionally employed in the art of formulation, and as described previously, for example, in WO2010/063700. Typically, when used for fungal control, 3-(difluoromethyl)-N-methoxy-1-methyl-N-[1-methyl-2-(2,4,6-trichloro-phenyl)ethyl]-1H-pyrazole-4-carboxamide is applied to useful plants via foliar application. However, in order to control nematodes, the preferred application methods are directly to the locus of said nematodes (e.g. the soil) or directly to plant propagation material.

As mentioned supra, in one aspect the invention provides a method of controlling a plant parasitic nematode, said method comprising applying an effective amount of 3-(difluoromethyl)-N-methoxy-1-methyl-N-[1-methyl-2-(2,4,6-trichloro-phenyl)ethyl]-1H-pyrazole-4-carboxamide, to the plant parasitic nematode, or to the locus of the plant parasitic nematode.

In one embodiment 3-(difluoromethyl)-N-methoxy-1-methyl-N-[1-methyl-2-(2,4,6-trichloro-phenyl)ethyl]-1H-pyrazole-4-carboxamide, is applied to soil and the method is used to control plant parasitic nematodes that are located in the soil. For example, the compound may be introduced directly in the soil on which a useful plant grows or the locus of the useful plant is treated with a liquid or solid preparation of the compound. This treatment may occur before planting or after planting. The compound may be applied by spraying or by using a drench system or a drip system, or may be in a granulated formulation suitable to be ploughed into the soil, or in the case of rice such granules may be metered into the flooded paddy field.

Typical rates of application per hectare is generally 1 to 2000 g of active ingredient per hectare, in particular 10 to 1000 g/ha, preferably 10 to 600 g/ha, more preferably 30 to 300 g/ha, and most preferably 40 to 200 g/ha.

In a further embodiment, 3-(difluoromethyl)-N-methoxy-1-methyl-N-[1-methyl-2-(2,4,6-trichloro-phenyl)ethyl]-1H-pyrazole-4-carboxamide is applied to plant propagation material (such as seeds) in the form of a nematicidal formulation. This formulation may contain one or more other desirable components including but not limited to liquid diluents, binders to serve as a matrix for the compounds as described herein, fillers for protecting the seeds, and plasticizers to improve flexibility, adhesion and/or spreadability of the coating.

The nematicidal formulation that is used to treat plant propagation material may be in the form of a suspension; emulsion; slurry of particles in an aqueous medium (e.g., water); wettable powder; wettable granules (dry flowable); and dry granules. If formulated as a suspension or slurry, the concentration of 3-(difluoromethyl)-N-methoxy-1-methyl-N-[1-methyl-2-(2,4,6-trichloro-phenyl)ethyl]-1H-pyrazole-4-carboxamide in the formulation is preferably about 0.5% to about 99% by weight (w/w), preferably 5-40%.(w/w).

The compound 3-(difluoromethyl)-N-methoxy-1-methyl-N-[1-methyl-2-(2,4,6-trichloro-phenyl)ethyl]-1H-pyrazole-4-carboxamide or the nematicidal formulation thereof may be applied to seeds by any standard seed treatment methodology, including but not limited to mixing in a container (e.g., a bottle or bag), mechanical application, tumbling, spraying, and immersion. Any conventional active or inert material can be used for contacting seeds with the compounds as described herein a, such as conventional film-coating materials including but not limited to water-based film coating materials such as Sepiret (Seppic, Inc., Fairfield, N.J.) and Opacoat (Berwind Pharm. Services, Westpoint, Pa.).

3-(Difluoromethyl)-N-methoxy-1-methyl-N-[1-methyl-2-(2,4,6-trichloro-phenyl)ethyl]-1H-pyrazole-4-carboxamide may be applied to a seed as a component of a seed coating. Seed coating methods and compositions comprising the compounds as described herein are encompasses in the present invention. Non-limiting examples of coating methods and apparatus for their application which are useful for use with the compounds as described herein are described in EP 0 963 689, U.S. Pat. No. 5,891,246, EP 0 652 707, GB 2 207 035, U.S. Pat. No. 5,107,787, and EP 0 245 731. Seed coating compositions are described, for example, in U.S. Pat. No. 5,939,356, EP 0 758 198, U.S. Pat. Nos. 5,876,739, 5,791,084, WO9702735, U.S. Pat. No. 5,580,544, EP 0 595 894, EP 0 378 000.

Useful seed coatings contain one or more binders and at least one of the compounds or at least two of the compounds as described herein. Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

It is preferred that the binder be selected so that it can serve as a matrix for the compounds as described herein. While the binders disclosed above may all be useful as a matrix, the specific binder will depend upon the properties of the compounds as described herein. The term "matrix", as used herein, means a continuous solid phase of one or more binder compounds throughout which is distributed as a discontinuous phase the compound 3-(difluoromethyl)-N-methoxy-1-methyl-N-[1-methyl-2-(2,4,6-trichloro-phenyl) ethyl]-1H-pyrazole-4-carboxamide. Optionally, a filler and/ or other components can also be present in the matrix. The term matrix is to be understood as including anything that may be viewed as a matrix system, a reservoir system or a microencapsulated system. In general, a matrix system consists of one or more compounds as described herein and filler uniformly dispersed within a polymer, while a reservoir system consists of a separate phase comprising 3-(difluoromethyl)-N-methoxy-1-methyl-N-[1-methyl-2-(2,4,6-trichloro-phenyl)ethyl]-1H-pyrazole-4-carboxamide, which is physically dispersed within a surrounding, rate-limiting, polymeric phase. Microencapsulation includes the coating of small particles or droplets of liquid, but also to dispersions in a solid matrix.

The amount of binder in the coating can vary, but will be in the range of, from about 0.01 to about 25% of the weight of the seed, more preferably from about 0.05 to about 15%, and even more preferably from about 0.1% to about 10%.

As mentioned above, the matrix can optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids, which may be used, include calcium bentonite, kaolin, china clay, talc, perlite, mica, vermiculite, silicas, quartz powder, montmorillonite and mixtures thereof. Sugars, which may be useful, include dextrin and maltodextrin. Cereal flours include wheat flour, oat flour and barley flour. The filler is selected so that it will provide a proper microclimate for the seed, for example, the filler is used to increase the loading rate of the compound as described herein and to adjust the control-release of said compound. The filler can aid in the production or process of coating the seed. The amount of filler can vary, but generally, the weight of the filler components will be in the range of about 0.05 to about 75% of the seed weight, more preferably about 0.1 to about 50%, and even more preferably about 0.5% to 15%.

The amount of 3-(difluoromethyl)-N-methoxy-1-methyl-N-[1-methyl-2-(2,4,6-trichloro-phenyl)ethyl]-1H-pyrazole-4-carboxamide that is applied to the seed will vary depending upon the type of seed, however, in general the amount applied to the seed will range from about 10 g to about 2000 g of the compound per 100 kg of the weight of the seed. In a particular embodiment, the amount of compound applied will be within the range of about 50 g to about 1000 g compound per 100 kg of seed. In another particular embodiment, the amount of compound applied will be within the range of about 50 g to about 600 g compounds per 100 kg of seed. In yet another particular embodiment the amount of compounds applied will be within the range of about 50 g to about 200 g of compound per 100 kg of seed weight. In yet another particular embodiment the amount of compounds applied will be within the range of about 50 g to about 100 g of compound per 100 kg of seed weight.

The invention also provides a method for treating, curing, controlling, preventing and protecting warm-blooded animals, including humans, and fish against infestation and infection by helminths, arachnids and arthropod endo- and ectoparasites which comprises orally, topically or parenterally administering or applying to said animals an anthelmintically, acaricidally or endo- or ectoparasiticidally effective amount of 3-(difluoromethyl)-N-methoxy-1-methyl-N-[1-methyl-2-(2,4,6-trichloro-phenyl)ethyl]-1H-pyrazole-4-carboxamide. The above method is particularly useful for controlling and preventing helminth, nematode, acarid and arthropod endo- and ectoparasitic infestations and infections in warm-blooded animals such as cattle, sheep, swine, camels, deer, horses, poultry, fish, rabbits, goats, mink, fox, chinchillas, dogs and cats as well as humans.

In the context of control and prevention of infestation and infections in warm-blooded animals, 3-(difluoromethyl)-N-methoxy-1-methyl-N-[1-methyl-2-(2,4,6-trichloro-phenyl) ethyl]-1H-pyrazole-4-carboxamide may be especially useful for the control of helminths and nematodes. Examples for helminths are members of the class Trematoda, commonly known as flukes or flatworms, especially members of the genera *Fasciola, Fascioloides*, Paramphistomu, *Dicrocoelium*, Eurytrema, Ophisthorchis, *Fasciolopsis, Echinostoma* and *Paragonimus*. Nematodes which may be controlled by 3-(difluoromethyl)-N-methoxy-1-methyl-N-[1-methyl-2-(2, 4,6-trichloro-phenyl)ethyl]-1H-pyrazole-4-carboxamide include the genera *Haemonchus, Ostertagia, Cooperia*, Oesphagastomu, Nematodirus, Dictyocaulus, *Trichuris, Dirofilaria, Ancyclostoma*, Ascaria and the like.

The compound 3-(difluoromethyl)-N-methoxy-1-methyl-N-[1-methyl-2-(2,4,6-trichloro-phenyl)ethyl]-1H-pyrazole-4-carboxamide may also control endoparasitic arthropod infestations such as cattle grub and stomach bot. In addition, acarid and arthropod ectoparasitic infestations in warm-blooded animals and fish including biting lice, sucking lice, bot flies, biting flies, muscoid flies, flies, myiasitic fly larvae, gnats, mosquitoes, fleas, mites, ticks, nasal bots, keds and chiggers may be controlled, prevented or eliminated by the compound. Biting lice include members of Mallophaga such as *Bovicola bovis, Trichodectes canis* and *Damilina ovis*. Sucking lice include members of Anoplura such as *Haematopinus eurysternus, Haematopinus suis, Linognathus vituli* and *Solenopotes capillatus*. Biting flies include members of *Haematobia*. Ticks include *Boophilus, Rhipicephalus, Ixodes, Hyalomma, Amblyomma* and *Dermacentor*. The compound 3-(difluoromethyl)-N-methoxy-1-methyl-N-[1-methyl-2-(2,4,6-trichloro-phenyl)ethyl]-1H-pyrazole-4-carboxamide may also be used to control mites which are parasitic on warm-blooded mammals and poultry including mites of the orders Acariformes and Parasitiformes.

For oral administration to warm-blooded animals, the compound may be formulated as animal feeds, animal feed premixes, animal feed concentrates, pills, solutions, pastes, suspensions, drenches, gels, tablets, boluses and capsules. In addition, the compound may be administered to the animals in their drinking water. For oral administration, the dosage form chosen should provide the animal with about 0.01 mg/kg to 100 g/kg of animal body weight per day of 3-(difluoromethyl)-N-methoxy-1-methyl-N-[1-methyl-2-(2, 4,6-trichloro-phenyl)ethyl]-1H-pyrazole-4-carboxamide.

Alternatively, 3-(difluoromethyl)-N-methoxy-1-methyl-N-[1-methyl-2-(2,4,6-trichloro-phenyl)ethyl]-1H-pyrazole-4-carboxamide may be administered to animals parenterally, for example, by intraruminal, intramuscular, intravenous or subcutaneous injection. The compound may be dispersed or dissolved in a physiologically acceptable carrier for subcutaneous injection. Alternatively, the compound may be formulated into an implant for subcutaneous administration. In addition the compound may be transdermally administered to animals. For parenteral administration, the dosage form chosen should provide the animal with about 0.01 mg/kg to 100 mg/kg of animal body weight per day of 3-(difluoromethyl)-N-methoxy-1-methyl-N-[1-methyl-2-(2,4,6-trichloro-phenyl)ethyl]-1H-pyrazole-4-carboxamide.

3-(Difluoromethyl)-N-methoxy-1-methyl-N-[1-methyl-2-(2,4,6-trichloro-phenyl)ethyl]-1H-pyrazole-4-carboxamide may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the compound. In addition, the compound may be formulated as ear tags for animals, particularly quadrupeds such as cattle and sheep.

3-(Difluoromethyl)-N-methoxy-1-methyl-N-[1-methyl-2-(2,4,6-trichloro-phenyl)ethyl]-1H-pyrazole-4-carboxamide may also be used in combination or conjunction with one or more other parasiticidal compounds (to broaden the spectrum of activity) including, but not limited to, anthelmintics, such as benzimidazoles, piperazine, levamisole, pyrantel, praziquantel and the like; endectocides such as avermectins, milbemycins and the like; ectoparasiticides such as arylpyrroles, organophosphates, carbamates, gamabutyric acid inhibitors including fipronil, pyrethroids, spinosads, imidacloprid and the like; insect growth regulators such as pyriproxyfen, cyromazine and the like; and chitin synthase inhibitors such as benzoylureas including flufenoxuron.

Such parasiticidal compositions will include a parasiticidally effective amount of 3-(difluoromethyl)-N-methoxy-1-methyl-N-[1-methyl-2-(2,4,6-trichloro-phenyl)ethyl]-1H-pyrazole-4-carboxamide or combinations thereof admixed with one or more physiologically tolerable inert, solid or liquid carriers known from veterinary medicinal practice for oral, percutaneous and topical administration. Such compositions may comprise further additives, such as stabilizers, antifoams, viscosity regulators, binders and tackifiers, whereas commercial products will preferably be formulated as concentrates, the end user will normally employ dilute formulations.

The present invention will now be described with reference to the following examples, which are by way of illustration and do not limit the scope of the invention in any way. The following examples demonstrate the ability of 3-(difluoromethyl)-N-methoxy-1-methyl-N-[1-methyl-2-(2, 4,6-trichloro-phenyl)ethyl]-1H-pyrazole-4-carboxamide to control nematodes.

EXAMPLES

Soybean Cyst Nematode (*Heterodera glycines*) on Soybean
Methodology for evaluating control of *Heterodera glycines* at all life stages on soybean in a greenhouse.

Five thousand *Heterodera* glycine eggs where placed in a 1 inch hole in the center of 3.5 inch×8 inch deep plastic pots. The seeds were inoculated first when applying the active compound as a seed treatment. The treated seed was placed in the center hole and covered up with sterilized top soil. Each pot was watered by hand, with approximately 50 mls of water applied to each pot once per day. 35 day after planting, the soil was gently rinsed from the roots of the emerged plants and place in a 20 mesh over a 60-mesh sieve. The root system was blasted with water to remove mature females. The 20-mesh sieve removed. The females were washed to the bottom of the 60-mesh sieve and rinsed into a tube for counting under a stereoscope. For root penetration experiments, the roots of the plants were removed from the pots at 7-14 days after planting, rinsed clean of soil, and stained with acid fuchsin stain. Stained nematodes in the roots were counted using an electronic stereoscope.

Series 1 Trials

| | | Trial 1: | | |
|---|---|---|---|---|
| Number | Treatment (Pydiflumetofen mg ai/seed) | Stained Juveniles w/l root | Mature SCN Cysts | Cysts per Gram of Root |
| 1 | Untreated | 30.0 | 28.0 | 213.6 |
| 2 | 0.0375 | 22.5 | 24.0 | 147.9 |
| 3 | 0.075 | 19.0 | 21.3 | 167.5 |
| 4 | 0.15 | 12.5 | 16.3 | 105.0 |

| | Trial 2: | | |
|---|---|---|---|
| Number | Treatment (Pydiflumetofen mg ai/seed) | SCN Within Root | Soybean Cyst Nematodes per Gram of Root |
| 1 | Check | 23.3 | 167 |
| 2 | 0.075 | 17.5 | 128 |
| 3 | 0.15 | 5.0 | 29.6 |

| | Trial 3: | |
|---|---|---|
| Number | Treatment (Pydiflumetofen mg ai/seed) | SCN Cysts per Root |
| 1 | Check | 18.3 |
| 2 | 0.15 | 10.4 |
| 3 | 0.30 | 5.5 |

| | Yield Data | |
|---|---|---|
| | Mean Difference in Yield Compared to Checks§ (Bu/Ac) | |
| Trial | Fluopyram (0.15 mg ai/seed) | Pydiflumetofen (0.075 mg ai/seed) |
| 4 | −3.5 | +3.0 |
| 5 | +5.4 | +3.7 |
| 6 | +2.9 | +7.5 |

Evaluation of Soybean Cyst Nematode
(*Heterodera glycines*) Egg Hatch

| Treatment | Concentration (ppm) | Percent Egg Hatch Reduction |
|---|---|---|
| Untreated Check | | — |
| Fluopyram | 100 | 61.9 |
| Fluopyram | 10 | 4.5 |
| Fluopyram | 1 | −1.3 |
| Pydiflumetofen | 100 | 64.0 |
| Pydiflumetofen | 10 | 34.7 |
| Pydiflumetofen | 1 | 4.7 |
| Fluensulfone | 100 | 0.5 |
| Fluensulfone | 10 | −1.5 |
| Fluensulfone | 1 | −2.1 |
| Tioxazafen | 100 | −0.9 |
| Tioxazafen | 10 | −0.5 |
| Tioxazafen | 1 | 0.4 |
| Burkholderia spp. | 100 | 1.7 |
| Burkholderia spp. | 10 | 0.0 |
| Burkholderia spp. | 1 | −1.6 |
| Bacillus amyloliquefaciens | 100 | 1.7 |
| Bacillus amyloliquefaciens | 10 | 2.5 |
| Bacillus amyloliquefaciens | 1 | −0.8 |
| Sodium hypochlorite 30% | | 100.0 |

Series 2 Trials

The action of pydiflumetofen against soybean syst nematode (SCN; *Heterodera glycines*) and its effect on soybean plants was assessed out as described previously, and compared to that of fluopyram. The number of SCN per stained root was counted, and the mean root weight per plant calculated, thus enabling the number of SCN per gram of root to be calculated.

Trial 1

| Test | Treatment (mg ai/seed) Pydiflumetofen | Treatment (mg ai/seed) Fluopyram | Mean SCN/ root | Root mass mean/ plant (g) | No. SCN/ g root tissue |
|---|---|---|---|---|---|
| 1 | — | — | 67.2 | 1.5 | 57.6 |
| 2 | 0.075 | — | 52.3 | 1.8 | 30.4 |
| 3 | 0.15 | — | 37.0 | 2.2 | 16.9 |
| 4 | 0.30 | — | 35.2 | 2.3 | 15.2 |
| 5 | — | 0.075 | 20.8 | 1.8 | 12.1 |
| 6 | — | 0.15 | 17.7 | 0.6 | 30.3 |
| 7 | — | 0.30 | 7.3 | 0.5 | 23.4 |

Root Knot Nematode (*Meloidogyne incognita*)
Methodology for Evaluating Root Knot Nematode Gall Count and Rating Process The roots of the plants were removed from the soil. The root system was then sprayed with water to remove remaining soil. The roots were spread out on a tray or counter top and the rate of galling or place each root system under a magnification light and count galls. For gall assessment ratings, a rating on a scale of 0-10 scale was given when compared against a standard gall rating chart. Gall count was also assessed.

Root Knot Nematode (*Meloidogyne incognita*) control - Soybean

| Treatment (Pydiflumetofen mg ai/seed) | Root Knot Nematode Galling (0-10 scale) | Root Knot Nematode Galls per Root |
|---|---|---|
| Untreated | 9 | 47.4 |
| 0.075 | 6.8 | 52.6 |
| 0.15 | 1.5 | 11.2 |

Multiple Nematode Species [Root Knot (*Meloidogyne incognita*); Spiral (*Helicotylenchus* Spp.) and Reniform Nematode (*Rotylenchulus reniformis*)]—Cotton

| | Juveniles per 100 cc s Soil | |
|---|---|---|
| Nematode Specie | Check | Pydiflumetofen (0.15 mg ai/seed) - measured 71 days after planting |
| Root Knot | 198 | 132 |
| Spiral | 258 | 254 |
| Reniform (juvenile) | 2264 | 1752 |
| Reniform (adult) | 6.8 | 2.8 |

Evaluation of Root Knot Nematode
(*Meloidogyne incognita*) Egg Hatch

| Treatment | Concentration (ppm) | Percent Egg Hatch Reduction |
|---|---|---|
| Untreated Check | | — |
| Fluopyram | 100 | 54.7 |
| Fluopyram | 10 | 55.9 |
| Fluopyram | 1 | 1.1 |
| Pydiflumetofen | 100 | 30.6 |
| Pydiflumetofen | 10 | 12.8 |
| Pydiflumetofen | 1 | 1.7 |
| Fluensulfone | 100 | 48.8 |
| Fluensulfone | 10 | −0.9 |
| Fluensulfone | 1 | −3.5 |
| Tioxazafen | 100 | 4.4 |
| Tioxazafen | 10 | −0.8 |
| Tioxazafen | 1 | −1.9 |
| Burkholderia spp. | 100 | 10.9 |
| Burkholderia spp. | 10 | 3.1 |
| Burkholderia spp. | 1 | −0.7 |
| Bacillus amyloliquefaciens | 100 | 2.6 |
| Bacillus amyloliquefaciens | 10 | −1.5 |
| Bacillus amyloliquefaciens | 1 | 2.1 |
| Sodium hypochlorite 30% | | 100.0 |

Lesion Nematode (*Pratylenchus brachyurus*) Efficacy—Soybean

Soybean plant roots were stained using acid fuchsin/methyl blue to assess for endoparasitic, endo/ectoparasitic, and semi endoparasitic nematodes that have entered the root system, using standard methodology.

| Treatment (Pydiflumetofen mg ai/seed) | Lesion Nematodes w/l root | Lesion Nematode per Gram of Root |
|---|---|---|
| Untreated | 44.7 | 162.1 |
| 0.0375 | 44.9 | 164.3 |
| 0.075 | 38.3 | 141.5 |
| 0.15 | 32.3 | 105.3 |

Reniform Nematode (*Rotylenchulus reniformis*) Efficacy—Soybean

Mean Difference in Soil Nematode Count Compared to Check

| Treatment | Nematode Reduction Compared to Check |
|---|---|
| 0.075 mg Pydiflumetofen/seed | −2912 |
| 0.15 mg Fluopyram/seed | −3146 |
| Aldicarb in-furrow (5.6 Kg/Ha) | −1937 |

Lance (Hoplolaimus Spp.) and Sting (*Belonolaimus longicaudatus*) Nematode

In Vitro Assay Measuring Dose Response of APN Against Sting and Lance Nematode.

| Species | Exposure Time (hours) | Percentage of Dead Nematodes | | | |
|---|---|---|---|---|---|
| | | Check | Pydiflumetofen Concentration | | |
| | | | 0.1 ppm | 10 ppm | 100 ppm |
| Lance | 1 | 0 | 12.7 | 37.9 | 74.8 |
| Lance | 24 | 0 | 68.5 | 81.6 | 23.9 |
| Lance | 48 | 0 | 41 d | 93.8 | 74.8 |
| Lance | 72 | 0 | 32.9 | 93.8 | 77.5 |
| Sting | 1 | 0 | 6.3 | 5.9 | 11.3 |
| Sting | 24 | 0 | 4.7 | 59.5 | 42.9 |
| Sting | 48 | 0 | 29.3 | 56.3 | 58 |
| Sting | 72 | 0 | 34.9 | 81.1 | 97.1 |

Lesion Nematode (Pratylenchus Spp.) Control in Corn (*Zea mays*)

Corn root tissue was stained using acid fuchsin/methyl blue to assess for endoparasitic, endo/ectoparasitic, and semi endoparasitic nematodes that have entered the root system, using standard methodology. The effect of pydiflumetofen was compared to fluopyram.

| Treatment (mg ai/seed) | Lesion Nematodes within root system | Lesion Nematode per gram of Root |
|---|---|---|
| Untreated | 830 | 2,001 |
| 0.4 mg Pydiflumetofen | 302 | 389 |
| 0.5 mg Pydiflumetofen | 124 | 105 |
| 0.25 mg Fluopyram | 108 | 211 |

Not only did pydiflumetofen reduce nematode numbers, it also resulted in an increase in corn shoot and root mass over that observed for untreated and fluopyram treated corn plants.

The invention claimed is:

1. A method of controlling infestation of a useful plant by a plant parasitic nematode, comprising applying pydiflumetofen to a plant seed of the useful plant prior to planting at a rate of 0.0375 to 0.15 mg per seed.

2. The method of claim 1, wherein pydiflumetofen is applied at a rate of 0.0375 mg per seed, 0.075 mg per seed, or 0.15 mg per seed.

3. The method of claim 1, wherein pydiflumetofen is in the form of a slurry of particles in aqueous medium.

4. The method of claim 3, wherein the concentration of pydiflumetofen in the aqueous slurry of particles is from 5% (w/w) to 40% (w/w).

5. The method of claim 1, wherein the plant seed is a soybean plant seed.

6. The method of claim 1, wherein the plant parasitic nematode is selected from the group consisting of the following species: *Heterodera* and *Meloidogyne*.

7. The method of claim 6, wherein the plant parasitic nematode is *Heterodera*.

8. The method of claim 6, wherein the plant parasitic nematode is *Meloidogyne*.

9. The method of claim 6, wherein the plant seed is a soybean plant seed.

10. The method of claim 1, wherein pydiflumetofen is applied at a rate of about 0.0375 mg per seed, about 0.075 mg per seed, or about 0.15 mg per seed.

11. The method of claim 1, wherein the useful plant exhibits a degree of endogenous resistance to the plant parasitic nematode.

12. The method of claim 1, further comprising identifying the plant parasitic nematode in a growing medium of the useful plant.

13. The method of claim 12, further comprising planting a crop of the plant seed after the applying of pydiflumetofen to the plant seeds of the crop, and wherein the plant seed is a soybean plant seed and the crop of the useful plant provides an increase of at least 3 bushels per acre compared to an untreated control.

14. The method of claim 12, further comprising planting a crop of the plant seed after the applying of pydiflumetofen to the plant seeds of the crop, and wherein the plant seed is a soybean plant seed and the crop of the useful plant provides reduces SCN cysts by at least 15% compared to a control not having pydiflumetofen.

* * * * *